(12) United States Patent
Anttalainen

(10) Patent No.: US 7,586,090 B2
(45) Date of Patent: Sep. 8, 2009

(54) CELL STRUCTURE, DEVICE AND METHOD FOR GAS ANALYSIS

(75) Inventor: Osmo Anttalainen, Mikkeli (FI)

(73) Assignee: Environics OV, Mikkeli (FI)

( * ) Notice: Subject to any disclaimer, the term of this patent is extended or adjusted under 35 U.S.C. 154(b) by 26 days.

(21) Appl. No.: 12/069,296

(22) Filed: Feb. 8, 2008

(65) Prior Publication Data

US 2008/0149823 A1    Jun. 26, 2008

Related U.S. Application Data

(62) Division of application No. 10/509,198, filed as application No. PCT/FI03/200226 on Mar. 25, 2003, now Pat. No. 7,339,162.

(30) Foreign Application Priority Data

Mar. 25, 2002    (FI) .................................. 20020565

(51) Int. Cl.
    *H01J 49/40*    (2006.01)
(52) U.S. Cl. ................. 250/282; 250/281; 250/288; 250/286
(58) Field of Classification Search ................. 250/282, 250/281, 288, 286
    See application file for complete search history.

(56) References Cited

U.S. PATENT DOCUMENTS 3,688,106 A    8/1972    Brain
4,193,296 A    3/1980    Janka
4,393,719 A    7/1983    Wiegand et al.
5,455,417 A *  10/1995   Sacristan ..................... 250/287
5,475,217 A    12/1995   Bradshaw
5,701,009 A    12/1997   Griffiths et al.
7,045,776 B2   5/2006    Kaufman et al.
7,211,791 B2   5/2007    Miller et al.
7,339,162 B2 * 3/2008    Anttalainen ................. 250/281

FOREIGN PATENT DOCUMENTS

| FI | 75005 | 12/1987 |
|----|-------|---------|
| FI | 96903 | 5/1996 |
| WO | WO 87/07720 | 12/1987 |
| WO | WO 92/07255 | 4/1992 |
| WO | WO 94/16320 | 7/1994 |
| WO | WO 01/69217 A2 | 9/2001 |
| WO | WO 01/69217 A3 | 9/2001 |

* cited by examiner

*Primary Examiner*—Nikita Wells
(74) *Attorney, Agent, or Firm*—Patterson, Thuente, Skaar & Christensen, P.A.

(57) ABSTRACT

The invention relates to a gas analysis based on the mobility of ions. The invention relates to a cell structure of an analysis device, the cell structure comprising the reference cell (201), the ionisation section (202) and the analysis cell (203) for identifying the electric mobility of ions. The invention also relates to a method for identifying the ions. Further, the invention relates to a system for identifying the ions.

13 Claims, 4 Drawing Sheets

US 7,586,090 B2

CELL STRUCTURE, DEVICE AND METHOD FOR GAS ANALYSIS

RELATED APPLICATION

This application is a division of application Ser. No. 10/509,198 filed Jun. 29, 2005, now U.S. Pat. No. 7,339,162 which claims priority to Application No. PCT/FI2003/200226 filed Mar. 25, 2003, which claims priority to Application. No. FI 20020565 filed Mar. 25, 2002, each of which is hereby fully incorporated herein by reference.

OBJECT OF THE INVENTION

The invention relates to analysis technique used in spectrometry based on the mobility of ions. The invention especially relates to a cell structure used in the analysis technique of gas, as disclosed in the preamble of the independent claim concerning it. The invention also relates to a device for identifying the substances in flowing gas, as disclosed in the preamble of the independent claim concerning it. The invention also relates to a system for identifying the substances in sample gas, as disclosed in the preamble of the independent claim concerning the system. Further, the invention relates to a method for identifying the substances in flowing sample gas, as disclosed in the preamble of the independent claim concerning it. The invention also relates to a method for measuring the sample gas velocity, as disclosed in the preamble of the independent claim concerning it.

DESCRIPTION OF THE TECHNICAL BACKGROUND

Of the structural units of gas, atoms and/or molecules formed by them as well as ions may be mentioned. A single ion or some other structural unit in the gas can momentarily move with a deviating speed and/or to a direction deviating from the flowing direction and/or speed of the gas itself, but on average, a single ion or some other structural unit of the gas in it, however, moves along with the gas. Also short-lived radicals can occur in the gas. Some molecules of the gas can also form loose clusters with polar molecules so that the bond between them is smaller, compared to the strength of a chemical linkage.

A gas sample is a sample to be taken from gas, estimated to represent the gas, from which the sample is taken, with a certain accuracy. A sample gas is a gas, the composition of the gaseous components of which represents the gas sample. The gas sample can also be an aerosol, in which case, in addition to the gaseous phase of the actual sample gas, there may also be present particulate bodies, in a macroscopic sense small pieces, particles, comprising other phases.

Identifying a gas on the basis of certain properties of its structural units can be performed with electrical methods provided that there is a sufficient amount of the structural units of the gas in the ionised state. At least two techniques are known for identifying ions from flowing gas with electrical methods, the IMS technique and the Drift tube, of which also the name drift technique is used. In the IMS technique, ions are analysed from a gas flow, which travels between such measuring electrodes that form an open aspiration condenser. The aspiration condenser has an electric field, the direction of which is perpendicular to the direction of the flow. The electric field deviates ions from the gas flow onto a plate of the aspiration condenser. The flight time and/or flight range of the ions is measured so that it is possible to separate the mobility of ions.

In the Drift technique, ions move in the electric field from a collection lattice to a measuring electrode, from which the magnitude of electric current is measured as a function of time. The zero point for each measurement is set to the zero point of the lattice pulse to be given to the collection lattice, and the ions to be measured move to the measuring electrode usually through a carrier gas with suitable properties. Due to its principle, separate circulations are generally needed for the sample and the carrier gas in the practical realisation of the Drift technique so that the cell is inevitably of a closed structure, as is also the case with the gas circulation.

An IMS technique is known, in which an open cell according to the simplified schematic diagram shown in FIG. 1 is used in the measurement of the sample gas mobility. The cell has an input at the first end of the analysis chamber 106, the gas sample flow 100 going to which is illustrated by an arrow. The chamber 106 itself is restricted by the plates 102 and 108. The cell has an electrode pair consisting of the electrodes 103 and 104 for detecting the ions 101 in the gas sample flow 100. The electrode 103 is attached to the plate 102 and the electrode 104 to the plate 108. The electrode 103 has a certain potential and the electrode 104 a certain second potential. The potential of the electrode 104 is generally close to the ground potential for placing the electric field 105 between the electrodes 103 and 104 and, on the other hand, for generating the voltage signal to be generated against the ground potential. The cell shown in FIG. 1 operates so that, as the gas ion 101 arrives at the space between the electrodes along with the gas sample flow 100, the electric field 105 interacts with the ion 101, in which case the interaction force causes a change of the travelling direction of the ion 101 and, in a certain case, its aggregation to the plate 104 so that the change of charge caused there by the aggregating ions is detectable as an electric current and changeable, for example, to a voltage signal. In cell solutions according to FIG. 1 for identifying gas on the basis of the mobility spectrum of its ions, an alternating voltage of nominally constant value can be used for providing the electric field 105 changing along with it. In this case, the strength of the electric field 105 can be varied, for example, sinusoidally, and/or several such electrode pairs as the pair formed by the electrodes 103 and 104 is used for analysing the charged particles so that the pairs are also attached to the cell limited by the plates 102 and 108 and mounted sequentially, following one another in the direction of flow so that there is an angle, generally a right angle between a mean velocity vector of the sample gas flow 100 and the directional vector of the electric field 105. For example, ions with certain mobility can then be picked up to the plate 104, and slightly different ions can be picked up to a similar second plate for forming the mobility spectrum, and the sample gas can be identified with the help of it.

Cell geometries are also known, in which an electric current caused by ions is detected by electrodes at opposite ends of the chamber so that the angle between the gas flow and the average direction of travel of the ions is approximately 180 degree. The gas in the drift chamber of the cell can, be let to drift through the drift chamber, for example, with the help of the flow; in some solutions however, also to the opposite direction from the average movement of the ions under the forces created by the electric field.

In the known technique, the incoming sample is charged substantially immediately, and the ions are let to drift along with the flow passing through the chamber but, on the other hand, according to the direction determined by the electric field; in some cases, also deviating from the direction, nevertheless, towards the current target or a respective electrode 104 for collecting the ions, which can also be located, for example, at the opposite end of the analysis chamber from the sample input arranged for sampling. When hitting such a current target as the electrode 104, the ion causes a change of the electric charge in it, which is interpreted as a current signal and processed into a suitable form with signal processing means.

Charging the gas sample can be performed in many different ways. Radioactive sources, light and corona discharge may be the best known charging techniques as such so that the facts generally known about charging depend on the charging mechanism desired to be used and/or on the purpose of use of the charged material, as has been explained in publications dealing with the known technology.

However, the known state-of-the-art cell structure has drawbacks. One of these is connected to the structure of the condenser formed by the electrodes. In the condenser, the change of potential on the plate 103 can be seen in the measurement made from the plate 104. In addition, variations in air humidity and temperature have a detrimental influence on the properties of the condenser, which makes the processing of the current signals caused by the ions more difficult and thus causes uncertainty in the forming of the mobility spectrum, which makes the identification more difficult.

Known IMS technique is described in a patent publication U.S. Pat. No. 5,455,417, the device according to which is illustrated by the cross-sectional drawing in FIG. 1B: The gas entering from the input 128 is heated in constant temperature with the help of the aluminium part 119, which contains the heater 127 controlling its temperature. The gas is charged with the help of the radioactive source 129, after which the gas advances to the analysis cell 125 having the plate electrode 121 and front electrode 122 and collection electrode 123 for the stepwise adjustment of a certain voltage and thus an electric field between the electrodes 121, 122 and 123, as is explained in the patent publication. By using the electric field in the way mentioned, it has been attempted to make the conventional aspiration condenser in FIG. 1B work in a more perfect manner. Among others, the temperature sensor used in the adjustment of temperature, the gas output 120 and the circuit boards 124 and 126 have been drawn to FIG. 1B, electronic components having been drawn to the surface of the latter circuit board 126.

The patent publication also discloses a method related to the technique, in which a sample including the substance to be analysed, the analyte, is first collected and charged. However, the patent specification mentions that, in this case, the concentration of the analyte has to be sufficiently high in the sample in order to achieve a saturation stage in the charging. The mobility of ions is determined from the charged gas sample. The concentration of the analyte in the sample is determined on the basis of the mobility.

The technique has its drawbacks. The massive aerosol particles advancing to the analysis cell 125 after the accumulator can get through the field formed by the electrodes 121 and 122, and most disadvantageously, cause considerable signal distortion on the analysis electrode 123, especially if and when they can carry a considerable electric charge. Further, the possible presence of aerosol particles in the accumulator can have a detrimental effect on the later stages, such as the mechanical and/or electrical blocking of the next analysis chamber, in which case the operation is made more difficult, and the reliability of the analysis result suffers. The possible re-suspension and/or related contact charging can also detrimentally transfer the charge to a wrong place. Another matter is related with heating. Namely, when transferring from heated sections to colder sections, the changes in temperature can cause phase transitions from gas phase to liquid phase and/or solid phase. In this case, the phenomenon in question is the forming of particles, nucleation, which has several subtypes, depending on the starting points of the particle formation. Especially the ion-induced nucleation triggered by radiation and, for example, the heterogenic nucleation taking place in structural defects on surfaces can in some circumstances cause the formation of particle-shaped material and its aggregation to places detrimental for the identification of ion mobility.

State-of-the-art solutions are further limited by a certain slowness in the changes of voltage so that it is also possible that changes occurring in the sample gas during a single measurement can influence the final result.

SHORT DESCRIPTION OF THE INVENTION

The object of the invention is to avoid the drawbacks according to the state of the art. Further, the object of the invention is to eliminate the drawbacks the variations in air humidity and temperature cause to the identification of ions. In addition, the object of the invention is to achieve a system, which makes possible the efficient reporting of measurement results. The object of the invention is further to provide a gas measuring device with the structure according to the invention. In addition, it is the object of the invention to provide a method for using the structure according to the invention in the mobility analysis of ions.

The objects of the invention are achieved with such a structure of a gas measuring device, which has a cell structure comprising a reference section, an ionisation section and an analysis section in said order, as arranged in the direction of flow of the gas to be measured.

The cell structure according to the invention is characterised in that, which is disclosed in the characterising part of the independent claim concerning the cell structure according to the invention.

The gas measuring device according to the invention is characterised in that, which is disclosed in the characterising part of the independent claim concerning the gas measuring device according to the invention.

The method according to the invention for identifying substances in flowing gas, based on the electric mobility of ions, is characterised in that, which is disclosed in the characterising part of the independent claim concerning the method according to the invention, for identifying substances in flowing gas, based on the electric mobility of ions.

The system according to the invention for identifying substances in ion form from flowing gas on the basis of their electric mobility is characterised in that, which is disclosed in characterising part of the independent claim concerning the system.

The method according to the invention, for electrically determining the flow rate in an aspiration condenser, is characterised in that which is disclosed in the characterising part of the independent claim concerning the method according to the invention for electrically determining the flow rate in an aspiration condenser.

The dependent claims depict other advantageous embodiments according to the invention.

The cell structure according to the invention is arranged for identifying a substance in a carrier gas, based on the analysis on the gaseous state of the mobility spectrum characteristic to the substance. For producing the mobility spectrum, a sample, a gas sample, is taken from the carrier gas, led to the cell structure of the device according to the invention; a reference signal is generated on the basis of the sample; the gas sample is ionised; the ionised sample gas is analysed; an analysis signal is generated in the analysis, and the mobility spectrum of the ions is determined from the sample gas on the basis of the reference signal and the analysis signal.

The cell structure of the device according to the invention is open in a certain way, and it comprises a drifting chamber between the input for the gas sample and the output for the analysed sample gas, the drifting chamber containing a reference section, an ionisation section and an analysis section in said order in the direction of travel of the sample.

The reference section is arranged to the cell structure according to the invention for generating the reference signal. The reference section has the reference cell and in it an electrode pair, a reference electrode pair having a certain reference electrode for generating the reference signal on the basis of the charges of ions arriving to the reference electrode. In this case, the reference signal is intended to be formed for eliminating the factors depending on the environmental factors of an unionised sample and such capacitive phenomena from the final mobility spectrum of ions and thus from the analysis result that can have a certain detrimental influence on the analysis signal itself and thus on the result.

The ionisation section has an ionisator, a charger, for producing ions and for bringing them into contact with the gas parts intended to be charged. The still unionised sample, intended to be entered into the ionisation section, is charged in a certain way for forming ions into the sample.

The analysis section has an analysis cell and in it a pair of electrodes, a pair of analysis electrodes, containing an analysis electrode, which is arranged so that ions can be collected onto it with the help of an electric field, so that the changes in charge, forming onto an analysis electrode in a way determined by the mobilities of the ions, can be interpreted as a certain electric current signal. On the basis of said electric current signal and, on the other hand, also with the help of the reference signal, an ion mobility distribution in the sample can be formed so that the substance in the sample can be identified on the basis of its ion mobility distribution. The use of the reference electrode in the formation of the mobility distribution is advantageous in the elimination of the influence of environmental factors so that identifying the substance from the gas is reliable. In addition, by using the reference electrode pair, drawbacks caused by the condenser structure to the accuracy of the mobility spectrum can be eliminated.

The analysis device according to the invention has the cell structure according to the invention. The analysis device according to the invention also most preferably includes filter means for removing particulate material from the gas sample; in other words, for purifying the gas as to a sample gas. The filter means can, for example, comprise a HEPA-type filter, a membrane or fibre filter, an electric filter, an impactor, or some other filter for collecting particles, or a combination of these, arranged especially for removing heavy aerosol particles from the gas sample, which particles can carry several charges with them or otherwise have a detrimental influence on the analysis result.

The analysis device according to the invention can also comprise control means, for example, for controlling the operation of the ionisator. The analysis device according to the invention can have means for controlling the supply of the operating voltage of the reference electrode pair and/or analysis electrode pair. The analysis device according to the invention can also comprise certain first signal processing means for processing the signal intended to be transmitted from the reference electrode.

The analysis device according to the invention can also comprise second signal processing means for processing the signal intended to be transmitted from the analysis electrode. The first and second signal processing means can be functionally connected to comparison means, in connection of which also memory means can be provided.

In connection of the comparison means, there most preferably is a microprocessor for controlling the comparison means. The microprocessor can be physically separate from the comparison means. There can also be several microprocessors to be used in different tasks for achieving certain independence. A microprocessor can also be arranged so that it can be used for forming a control signal to the ionisator, to the means for forming the reference voltage and/or the means for forming the analysis voltage, for example, through specific control means either indirectly or directly by controlling said means and/or ionisator.

In a system according to an advantageous embodiment of the invention there is an analysis device having functional control means for controlling the analysis operation of the device by remote control, preferably wirelessly, for example, on the basis of data transmission occurring with the help of electromagnetic radiation, but possibly also through an electric and/or optical cable. In this case, the mentioned analysis device according to an embodiment of the invention, a remote device, most preferably contains transmitter means and receiver means, for example, combined as transmitter-receiver means, arranged for receiving the control signal controlling the operation of the analysis device and/or for transmitting the data describing the measurement results and the status of the remote device to a second device communicating with the remote device.

So it is possible, for example, to control the cell structure of the device according to the invention from the outside of the device wirelessly and/or with the help of a cable, the cell structure being placed, for example, to a fume hood or a similar place isolated from the environment in a certain way. When applicable, the control can be realised wirelessly and partly by cable.

SHORT ACCOUNT OF THE FIGURES

FIG. 1A illustrates a cell according to the known technique; and

FIG. 1B illustrates another cell according to the known technique.

Figure 1A:
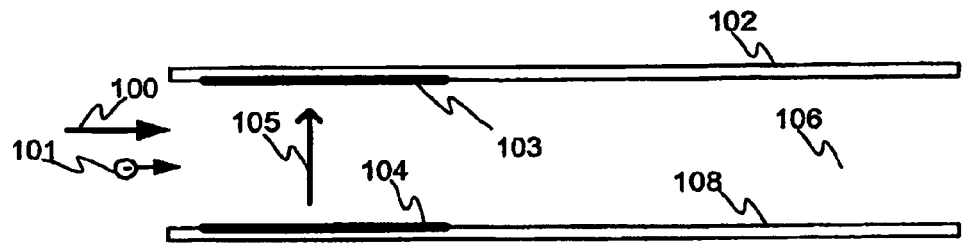
FIGS. 1A and 1B illustrate the known technique as follows.
Figure 1B:
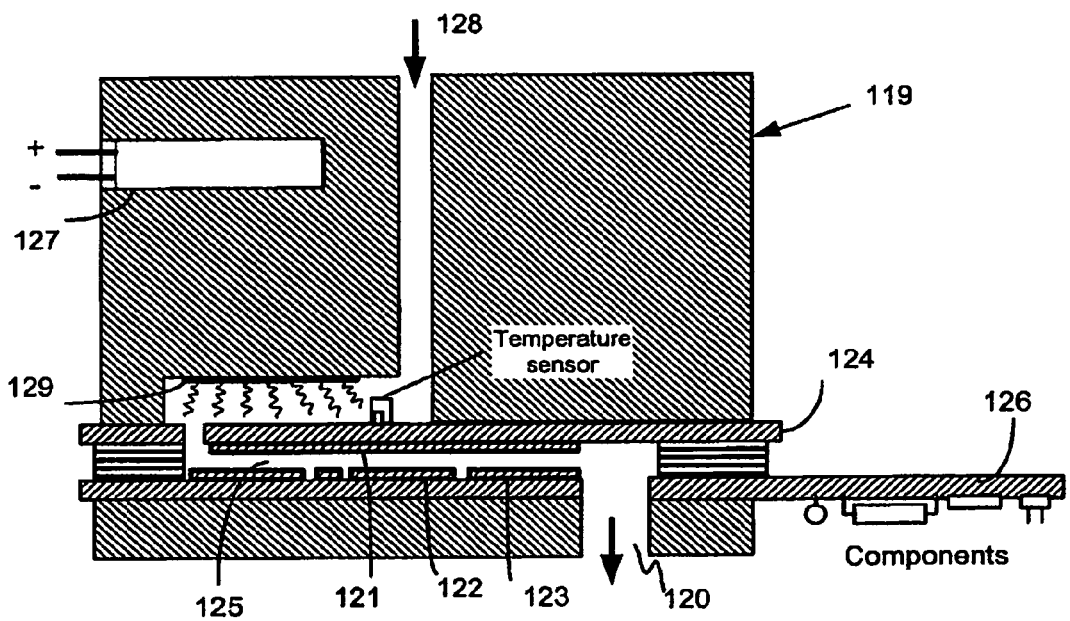
Figure 2:
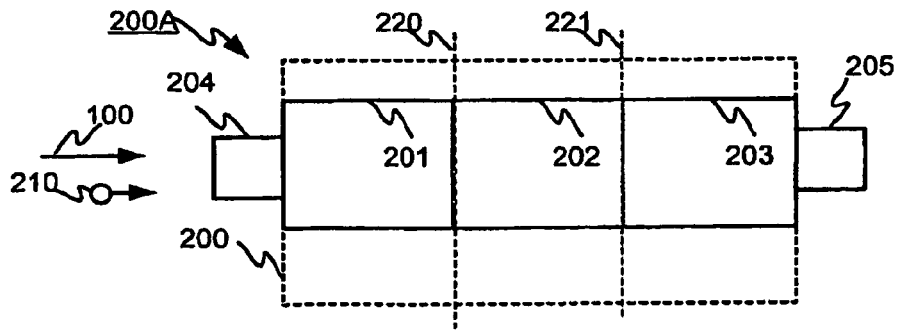
Figure 3A:
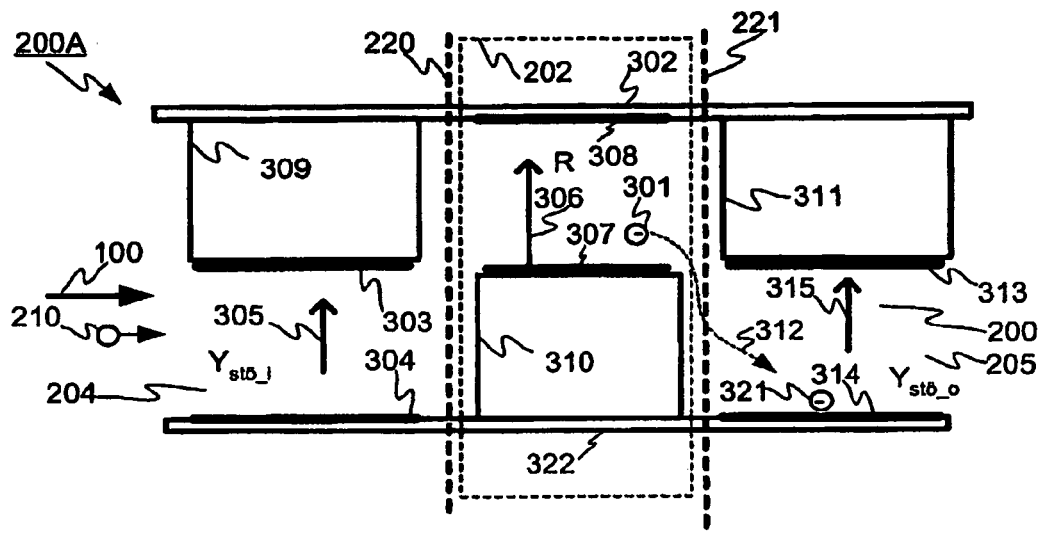
Figure 5:
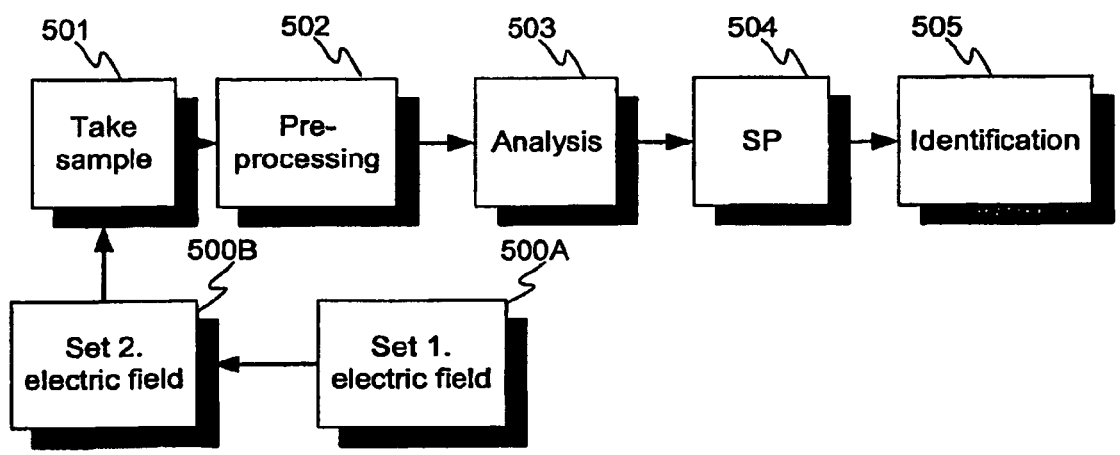
Figure 3B:
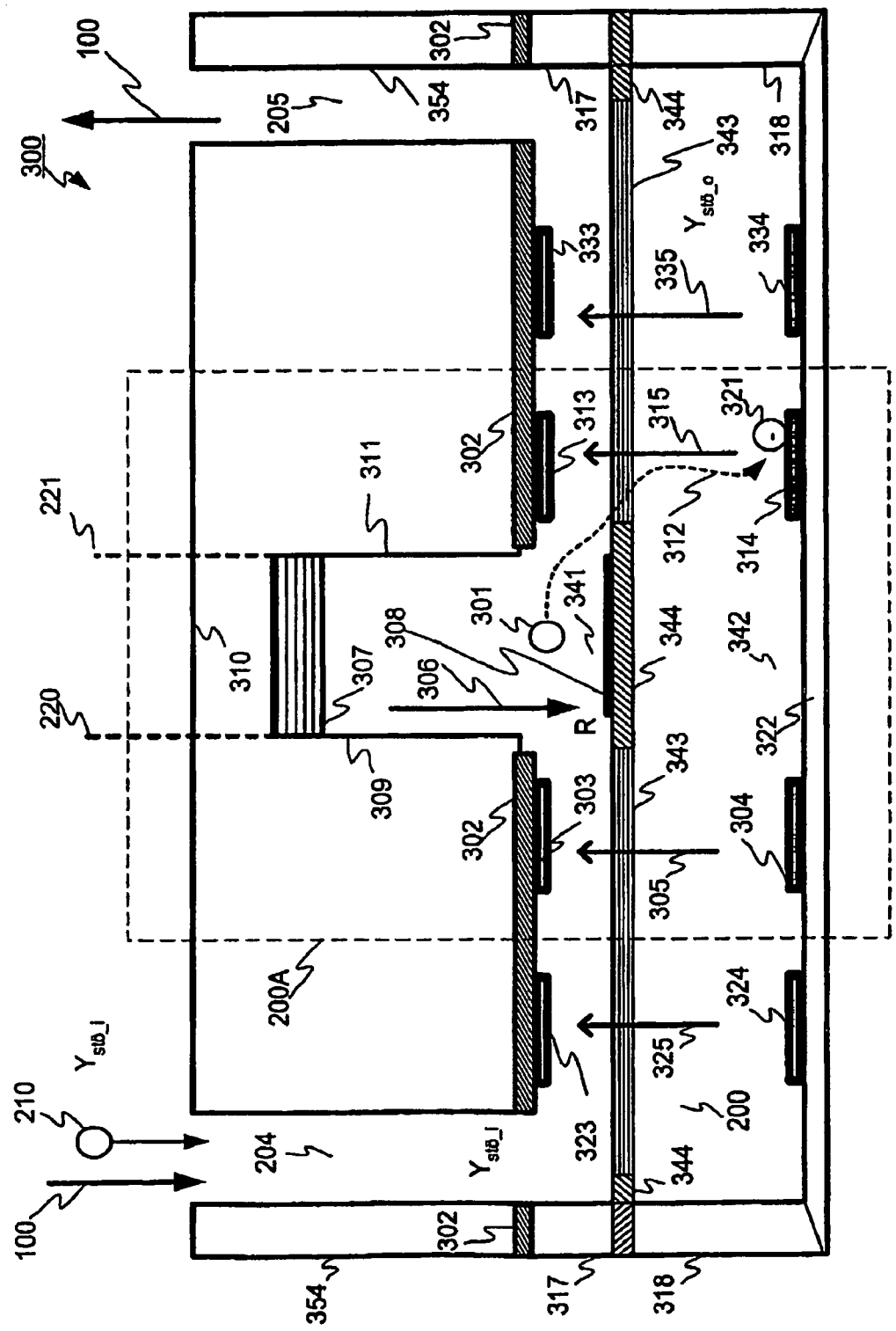
Figure 4A:
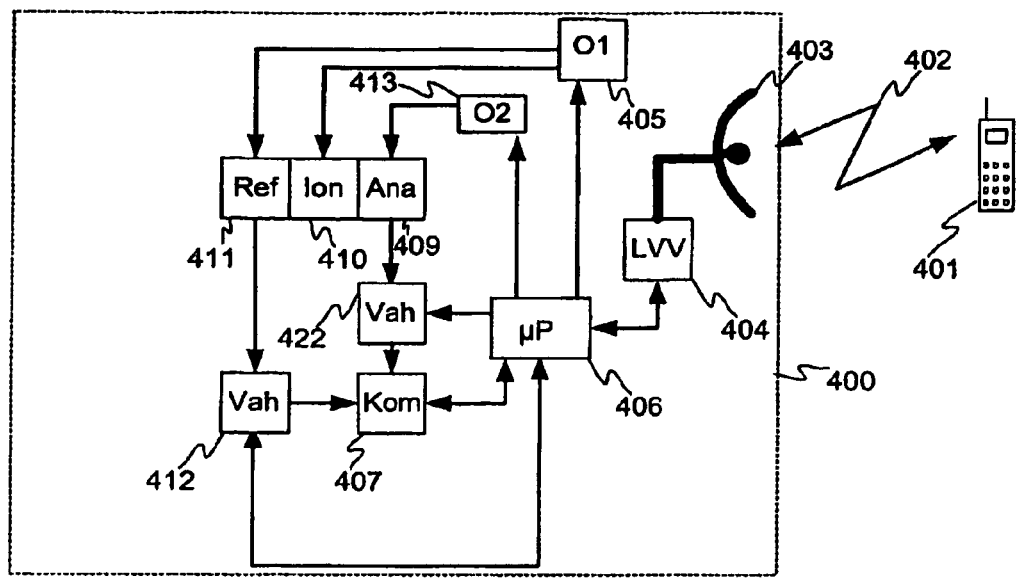
Figure 4B:
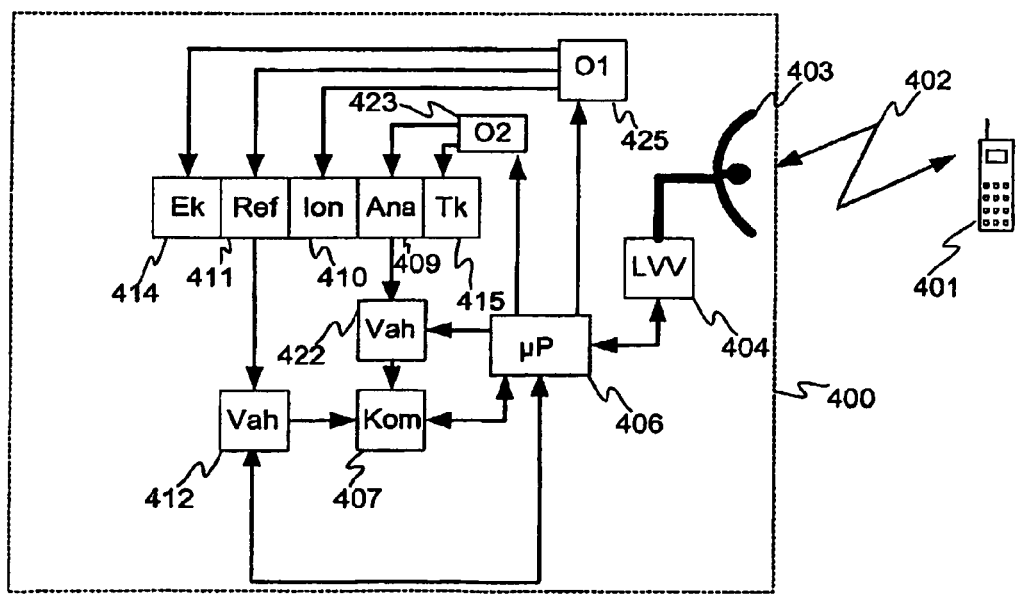

The invention is next explained in more detail, referring to the advantageous embodiments shown as examples and to the enclosed drawings 2-5, in which FIG. 2 illustrates as a diagram the cell structure of an advantageous embodiment according to the invention;

FIG. 3A illustrates a diagram for a first order cell structure according to an advantageous embodiment of the invention;

FIG. 3B illustrates a diagram for a second order cell structure according to an advantageous embodiment of the invention;

FIG. 4A illustrates a diagram for a gas measuring device according to an advantageous embodiment of the invention;

FIG. 4B illustrates a diagram for another gas measuring device according to a second advantageous embodiment according to the invention; and FIG. 5 illustrates a method according to the invention for identifying substances in flowing gas.

Same reference numbers and markings are used of corresponding parts in the Figures.

DETAILED DESCRIPTION OF ADVANTAGEOUS EMBODIMENTS ACCORDING TO THE INVENTION

A. First Advantageous Embodiment

FIG. 2 shows on a very coarse level an exemplary diagram of the cell structure 200A according to an advantageous embodiment of the invention. The cell structure 200A has a drifting chamber 200 for sample gas, one structural unit 210 of which has been drawn into the figure. The cell structure 200A, its drifting chamber 200, has the reference section 201, the ionisation section 202, and the analysis section 203. For illustrative purposes, the reference section 201 is separated from the ionisation section 202 by the vertical broken line 220. For illustrative purposes, the ionisation section 201 is separated from the analysis section 203 by the vertical broken line 221. The input 204 of the cell structure 200A for the gas sample flow 100 and the output 205 for the analysed sample gas are functionally located at different ends of the cell structure 200A so that the reference section 201, the ionisation section 202 and the analysis section 203 of the cell structure are located in said order in the direction of travel of the sample, irrespective of the possible bendings of the drifting chamber 200. On the basis of the diagram drawn in FIG. 2, the cell structure 200A has the substantially straight drifting chamber 200, but on the basis of what is shown in the invention, it is obvious for one skilled in the art that the sections of the drifting chamber 200 can also be arranged to bend, for example, for saving space, in which case the ends of the cell structure 200A can be located physically very close to each other.

It is stated that the cell structure according to an advantageous embodiment of the invention can be an open cell structure of first order, substantially according to the example in FIG. 3A. The cell structure according to another advantageous embodiment of the invention can be a cell structure of second order, substantially according to the example in FIG. 3B. FIG. 3A illustrates, more than FIG. 2 in detail, the internal structure of the cell structure according to an advantageous embodiment of the invention. The cell structure in FIG. 3A is an example of a first order cell structure. In FIG. 3A, for the illustrative purposes, also the vertical broken line 220 separating the reference section 201 from the ionisation section 202 and the vertical broken line 221 separating the ionisation section 202 from the analysis section are marked in the drifting chamber 200 of the cell structure 200A. Let it be stated that the separation indicated by the broken lines 220 and 221 is not desired to restrict the invention. If the ionisation section 202 has a radiation source, it may be preferable to separate it 202 from the reference section 201 and/or analysis section 203. In such case, there may also be physical equivalents present for the broken lines 220 and/or 221 in the drifting chamber 200 to prevent the ionising radiation originating to the ionisation section from influencing the sections separated from the ionisation section. In such a case, the separating wall corresponding to the broken line 220 can also have a bending geometry for allowing the travel of gas, on the one hand, and for simultaneously preventing the travel of radiation to other sections of the drifting chamber 200, on the other hand. Also the separating wall corresponding to the broken line 221 can have a bending or partly apertured geometry for allowing the travel of gas, on the one hand, and for simultaneously preventing the travel of radiation to other sections of the drifting chamber 200, on the other hand.

In FIG. 3A, the drifting chamber 200 has a section corresponding to the reference section 201, the reference cell, which is substantially located at the place of the reference electrode pair structure consisting of the reference electrodes 303 and 304. For separating certain electrodes in FIG. 3A from the plates 302, the electrode supports 309 and 311 of insulating material have been drawn to the Figure. They can also be integrated as part of the structure of the plate 302. The electrode 303 is intended to be connected, for example, via the voltage source 405 shown in FIG. 4A for arranging the electric field 305 between the electrodes 303 and 304. The voltage source is not shown in FIG. 3A. The electrode 304 is then substantially in constant potential close to the ground potential. As ions arrive at the electrode 304, the potential of the electrode 304 changes. The charge arriving with each arriving ion slightly changes the potential of the electrode 304 so that the changes of the electrode potential are relatively small per charge of an arriving ion. As ions arrive at the electrode 304, the changes of its charge can be detected as electric current. Most preferably the detection of changes of charge can be made with an electrometer or similar or, for example, with a suitable current-voltage converter. In this case, for detecting the changes of charge, the electrode 304 can be used as the sensor for the electrometer the changes of charge of which are detected. With the help of the current-voltage converter, an output signal of the electrometer can then be formed, and on the basis of it a reference signal, either directly or by processing, for example, a voltage signal in relative to the ground potential.

In an analysis situation, the electric field between the electrodes 303 and 304 of the reference cell can then be time-dependent, in which case the waveform describing the time dependency is most preferably sine, triangle or ramp, for providing a scanning electric field. In the invention it is not wanted to restrict the waveform of said electric field to any specific one, but the waveform can also be a so-called free waveform so that it can be presented as a series of terms to be formed with the help of an exponential functions. Also some other arrangements, known for one skilled in the art, can be used for detecting weak changes of charge and their converting into a current and/or voltage signal. Said kind of detection of a current and/or voltage signal based on the changes of charge can also be arranged to some other reference potential than relative to the ground potential. It may also naturally be arranged so that changes of charge are detected from the electrode 303 in a potential, which has a high absolute value in relation to ground, but taking into account the voltage between the electrodes 304 and 303 upon forming the actual desired signal can then require special arrangements. In the invention, it is not wanted to restrict the direction of the electric field 305 merely to the momentary case drawn to the Figure, but some other, a static field can be used, but also such an alternating field which has a momentary direction, an amplitude, frequency and/or waveform.

In FIG. 3A, the drifting chamber 200 also has the ionisation section 202 as in FIG. 2. In the diagram illustrated by FIG. 3A, the ionisation section is separated from the rest of the drifting chamber 200 by the broken lines 220 and 221. The ionisation section 202 is substantially restricted to the area limited by the electrodes 307 and 308. Electrodes 307 and 308 have been drawn in FIG. 3A, between which, for example, a corona discharge can be provided, by a controllable voltage source 405 (FIG. 4A), for example, so that it is possible to charge, produce ions 301 into the gas travelling in the area there between the electrodes 307 and 308 by an electric field.

For producing the ions 301, also an ionising field 306 can be used, which can be, for example, a radiation field provided by radiation generation resulting from of radioactivity, a radiation field based on ultraviolet radiation, and/or an electric field. An example illustrates the direction of the ionising field 306 by an arrow, for example as a direction of travelling radiation; but also such an ionising field can be used which has components to several directions, or the direction can be some other direction than the one shown by the arrow. When applicable, the electrodes 307 and/or 308 can then be replaced by a material or piece that produces radiation, for example, by a strip containing a radioactive substance. By using a radioactive charger and an electric field as a combination, it is also possible to restrict the access of so-called recoil atoms, resulting from radioactivity, to the sections located after the ionisation section in the cell structure and to thus improve the measuring itself.

FIG. 3A shows support 310 supporting the electrode 307. With the geometry of the support 310 and of the electrode 307, it is possible to influence also the range of radiation into other parts of the drifting chamber. The support 310 can also be shaped so that it further comprises limits for separating the ionisation section from the rest of the drifting chamber 200, corresponding, for example, to the separation indicated by the broken lines 220 and 221, for restricting the ionisation effect of the charger to a certain section of the drifting chamber. However, use of the support 310 is not necessary.

The radiation source can be located on the same level with some of the electrodes 304, 314, 303 and 313 listed as an example. In the first order cell structure it is also possible to locate the radiation source 308 to the other side of the plate 302 than in FIG. 3A, so that the radiation source can be structurally arranged to be, easily replaceable. In this case, the plate 302 itself and/or the separation radiation control plate intended to be attached to it has a set of holes of which at least one hole has a certain shape, at least one diameter and length as well as location in relation to the other holes for forming a certain pattern. The shape of the hole can then be angular, rectangle or circular, for directing the radiation, originating from the radiation source through said at least one hole to the ionisation section, in which the gas is travelling, for optimising the dose rate resulting to the gas in a most appropriate manner for the charging of the gas. With the shape of the holes, especially their length and cross-section perpendicular to the longitudinal direction and also the shape, it is possible to influence the distribution of radiation in the ionisation section. The same principle can also be applied to a second order cell structure so that the radiation source can be arranged to be modular and replaceable, for example, by fast couplings for connecting the radiation source and the radiation guiding plate to the charger section. In this case, it is possible to influence the directional pattern of radiation in a similar way as has been explained in connection of the first order cell structure.

In FIG. 3A, the drifting chamber 200 has a section corresponding to the analysis section 203, an analysis cell, which occurs co-located substantially at the analysis electrode pair consisting of the analysis electrodes 313 and 314. The electrode 313 is intended to be connected to voltage, for example, through the voltage source 413 (FIG. 4A) for arranging the electric field 315 between the electrodes 313 and 314. The voltage source is not shown in FIG. 3A. In this case, the electrode 314 is substantially in constant potential close to the ground potential. The charge arriving with each arriving ion slightly changes the potential of the electrode 314 so that the changes of potential of the electrode 314 calculated per one arriving ion are relatively small. As ions arrive at the electrode 314, its changes of charge can be detected as electric current. Most preferably, the detection of changes of charge is made with an electrometer or similar or, for example, with a suitable current-voltage converter. In this case, the electrode 314 can be used for detecting the changes of charge as the sensor for the electrometer the changes of charge of which are detected. It is then possible to form an output signal of the electrometer with the help or the current-voltage converter, and on the basis of it directly or by modifying an analysis signal, for example, a voltage signal in relation to the ground potential. Also, some other arrangement, known for a skilled man in the art, can be used for detecting weak changes of charge and for converting into a current and/or voltage signal. The detection of a current and/or voltage signal based on the said kind of changes of charge can also be arranged to some other reference potential than relative to the ground potential.

In an analysis situation, the electric field between the electrodes 313 and 314 can then be time-dependent, in which case the waveform describing the time dependency is most preferably sine, triangle or ramp, for providing a scanning electric field. It is not intended in the invention to restrict, the waveform of the electric field to any particular form, but the waveform can also be a so-called free waveform such that can be presented as a series of terms derivable form an exponential function. It may naturally also be arranged so that changes of charge are detected from the electrode 313 in a potential with a high absolute value relative to the ground, but when forming the actual desired signal, in such a case taking into account the voltage between the electrodes 313 and 314 can require special arrangements. In such a case, also some advantages achieved by the use of the reference cell may be partly lost in the determination accuracy of the mobility. It is not intended in the invention to restrict, the direction of the electric field 315 merely to the momentary case drawn in the Figure, but also some other, static electric field can be used, as well as alternating electric fields with a momentary direction, an amplitude, frequency and/or waveform.

In embodiments according to the invention, in the first order cell structure as well as in the second order cell structure, the dependency of the collection efficiency of ions on the electrode voltage between the cell electrodes is taken into account for the both, the analysis cell and the reference cell. Relating to the identification of ions, the dependency of the collection efficiency on the voltage between the electrodes of the cell can also be taken into consideration within other cells, such as a front cell and/or back cell, also in a first order cell structure with a front cell and/or back cell.

It is stated on the reference electrode and the analysis electrode that, by using one such electrode, a voltage signal can be formed as based directly on the change of said electrode in potential relative to the ground potential, but in such a case the possible influence of said change in potential on the collection efficiency of ions onto said electrode has to be considered.

As based on the gas velocity, it can be taken into account the moment of time, at which the momentary value of the reference signal has been formed with the help of the reference electrode. In such a case, a potential interference advancing with the gas into the analysis cell can be eliminated in a right phase from the signal used for analysing the ion mobility so improving the measurement accuracy.

The status of the gas flowing to the area of the reference electrode pair can be described by several physical quantities. In FIG. 3A, the physical state of the sample gas in a gas sample is illustrated, as the gas arrives at the reference section of the cell structure, by a first state vector $Y_{sto\_i} = Y_{sto\_i}(T, RH, S_i, \mu, \xi, r, ..$ ., N.sub.i), which has an finite number of components. A set of components of the state vector can then be described as follows: T=temperature of the gas or similar, RH=relative humidity, S.sub.i=the saturation ratio for the component i in the gas, mu..sub.xi=mass-absorption coefficient for the radiation type x with a component i in the gas, r=gas density, N.sub.i=molar fraction of the structural units of a component i in the gas. Most preferably, the sequence formed by the components of said state vector is free, i.e. the components of the state vector are not dependent on each other. In practice, for measuring technical reasons, it however may be necessary to select also such components to the sequence that one has to compromise with the freedom of the sequence. In addition to the ones mentioned, components of the first state vector can be the resistivity of a component i of the gas, viscosity, pressure, partial pressure, a mean free path of a gas molecule of the gas component i in certain pressure and temperature and with a fraction of a certain gas composition, diffusion coefficient and/or mechanical mobility of the type i of a gas molecule, and the turbulence/laminarity of the flow field. However, it is not intended in the invention to restrict into any certain combination of said quantities.

The flow state of the sample gas in the analysis section has been illustrated by a second state vector Y.sub.sto.sub.—.sub.o in FIG. 3A, which is the same as Y.sub.sto.sub.—.sub.i with a certain accuracy. By presuming that the first and second state vector are identical according to their reference components, the electric current detected on the analysis electrode 314 can be corrected by a correction to be formed on the basis of the electric current detected from the reference electrode 304, which can be formed, for example, on the basis of the reference signal. If the first and second state vectors are not identical with a sufficient accuracy, the difference can be taken into consideration by calibration.

Most preferably, the electric field 305 between the reference electrode pair has been arranged in the same way as the electric field between the analysis electrode pair, both in relation to the amplitude, strength and frequency and the phase, as is shown in the Figure. Nevertheless, it is possible to deviate from this, if it is only known how the deviation will influence the reference signal and thus the mobility spectrum of the ion under analysis so that the deviation can be taken into consideration in the identification of the substance in the sample. In this case it is also possible to take into account the possible influences on the state vector Y.sub.sto.sub.—.sub.i as the identification advances, also iteratively. It is also possible to compensate, for example, structural uncertainties caused by the manufacturing accuracy of mechanics, by using such a voltage source, in which it is possible to separately adjust the phase and amplitude of the voltage feeding the cell, most preferably independently from each other. Besides continuous adjustment, the adjustment can then also be understood to mean the setting of the limit for the adjustment area and the non-recurring set-up occurring in connection of the setting of the device using the cell structure to functional state, also in connection of a calibration of recurring nature.

In an embodiment according to the invention, the state vectors Y.sub.sto.sub.—.sub.i and/or Y.sub.sto.sub.—.sub.o have been stored to memory so that they can be used and/or updated on the basis of the measurement result in the measuring action performed after the actual calibration. In another embodiment according to the invention, the state vector is iterated during the measuring action on the basis of the results for specifying the analysis result.

As the ion 301 coming from the ionisation section passes in the drifting chamber 200 along the average route 312 of the ion 301 to the analysis section and in it within the reach of the electric field 315, it (315) deflects the travel of the ion 301 from the route 312 so that it 301 is passed to the electrode 314 where the ion 301 will stay to convey its charge to the electrode 314 as a second ion 311 passed there earlier that has not yet had time to convey all of its charge to the electrode 314. As the charge has been conveyed, the former ion can now leave the electrode 314 as a neutral molecule or similar or to react with the surface, either chemically by binding to it or, due to adhesion-type forces, to stay in some vacancy of some structure of the surface. One alternative for the former ion is to leave the drifting chamber 200 with and/or like the other gas particles.

In FIG. 3A, the ion 301 has been marked with a negative charge. According to a momentary situation, the route 312 of the ion in the electric field 315 has been drawn as directing away from the electrode 313 in FIG. 3A. The electric field is achieved between the electrodes 313 and 314 by coupling a voltage with a suitable polarity between them. If the charge of the ion 301 were opposite in relation to the one marked in the figure and, nevertheless, the electrode 313 were in a more negative potential than the electrode 314, the ion 301 would move towards the electrode 313. If again the direction of the electric field 315 were now changed to the direction of the arrow in the figure and back to opposite again, also the path of the ion in the analysis section changes, following the change of the electric field in a manner, which also depends on the electric mobility of the ion 301.

The electric field 315 can consist of an electric field of a constant value and/or such an alternating electric field, which has a certain direction, amplitude and frequency suitable for the appropriate purpose so that, for example, ions with a certain mobility can be picked onto the electrode 314.

In such a case, it is also possible to arrange a certain temporal duration to the electric field, and to vary its temporal duration so that different kinds of control conditions can be realised to be utilised in the defining of ion mobility. The voltage between the electrodes in the reference electrode pair has to follow the voltage between the electrodes in the analysis electrode pair in a certain way. Most preferably the fields of the reference cell and the analysis cell have the same phase, frequency and amplitude, as the electrodes have similar mechanical dimensions. The similarity must then be understood to mean similarity with a certain manufacturing-technical accuracy, and the same phase so that delays caused by the flow of gas and/or functions of electronics have been taken into account in the integration.

An embodiment, according to the invention, comprises a reference electrode, which has been disintegrated into sub-electrodes. In this case, the sub-electrodes operate under a same control so that said control to each sub-electrode is dependent on, but not necessarily the same as the control of the sub-electrodes of some other disintegrated reference electrode. Separate sub-signals can be formed from the subelectrodes, which can be processed separately and/or summed in a suitable way in a suitable phase for providing a total signal, ultimately aimed for improving the accuracy of the mobility analysis.

An embodiment, according to the invention, contains such electrode pairs as the electrode pair consisting of the reference electrodes 303 and 304, reference electrode pairs, sequentially in the flow direction of the sample in the reference section of the drifting chamber. In this case, the electrodes of the reference electrodes that operate for receiving the ion charges, such as the electrode 304, do not have to be equally long in relation to each other in the travelling direction of the sample, but they can also be of different lengths and/or different shapes, even of different widths. Advantage can then be achieved by varying the electric conditions used for the determining of mobility.

One advantageous embodiment according to the invention contains such electrode pairs as the electrode pair consisting of the analysis electrodes 313 and 314, analysis electrode pairs, sequentially in the flow direction of the sample in the analysis section of the drifting chamber. In this case, the electrodes of the analysis electrodes that operate for receiving the ion charges, such as the electrode 314, do not have to be equally long in relation to each other in the travelling direction of the sample, but they can also be of different lengths and/or different shapes, even of different widths.

However, it can be stated that the electric properties of the reference electrode pair and the analysis electrode pair have to be identical with a certain accuracy for obtaining the best possible benefit of the use of the reference electrodes. According to the inventional idea it is, however, possible to also use non-identical reference and analysis electrode pairs, but in this case, the differences in the their electric properties caused by the non-identicality are of such a nature that they can be taken into account with a certain accuracy when forming reference and/or analysis electrode pairs. As an example of said possible differences between the electrode pairs, the distance between the electrodes in the electrode pair, their shape and size, and also material, especially surface material, are given. The surface material also has an important role when the electric properties of different electrodes are evaluated in a long time interval. Namely the electrode surfaces, for example, when they are made of metal, have a tendency to form compounds with certain components of the gas sample so that the conductivity properties can change on the electrode surfaces along with time. In addition, in some especially disadvantageous conditions of use, the particulate substances can find their way in one form or another to some electrode surfaces so that, when depositing to these, the particulate-substances can also change the conductivity properties of the electrode surface, to which it settles.

B. Second Advantageous Embodiment

FIG. 3B discloses an example of a second advantageous embodiment according to the invention, as a second order cell structure 300. In FIG. 3B, there is outlined with a closing broken line the area which for the main part substantially contains a first order cell structure 200A according to FIG. 3A, which cell structure however deviates in its geometry from the cell structure shown in FIG. 3A with regard to the arrangement of ionisation, the ionisation section being nevertheless substantially between the reference section and the analysis section as in FIG. 2. It can also be stated that the cell structure 200A in FIG. 3A differs from the cell structure 300 in FIG. 3B with regard to the divider plate, which is indicated with the reference numbers 344 and 343, and in which the part 344 refers to the uniformly closed section of said divider plate, and the part 343 to such a section of the same divider plate, which is provided with an aperture or several apertures. The part 343 of the divider plate with apertures is most preferably arranged at an electrode pair, the electrode pair containing a first electrode 303, 313, 323, 333, and a second electrode 304, 314, 314, 334. The divider plate functions as to distribute the flow in the second order cell structure to parts, to the one of which ionisation effect is directed and to another one of which not. With the design of the divider plate it is possible to influence the profile of the gas flow. The divider plate can be flat, but it can have a certain design in a certain part for forming the flow profile of the gas flow; however, in the end, for optimising the mobility analysis. In this case, advantage may be gained by the design, especially at the place of the input aperture and/or the input of the ionisation section, or in other places in which the geometry and thus the profile of the gas flow can change. For example, the divider plate can be provided with suitable design for the ionisation section for achieving a sufficient input flow. It can further be stated that it is possible to use the different designs of the divider plate to influence the mixing of gas, either in a balancing or promoting manner. The design of the divider plate can also be used for influencing the flow quality in the vicinity of the formed section of the divider plate, whether it is turbulent, laminar, or in a transition regime there between.

The closed part 344 of the divider plate is most preferably arranged at the ionisation section to prevent ionisation effect on the part of the sample gas that passes through the drifting chamber 200 along its part 342 past the ionisation section. If the radiation field 306 is used for achieving ionisation, the material and/or material strength of the divider plate shall then be most advantageously selected according to the components of the radiation field 306 so that the ionisation effect is minimised in the part 344 of the divider plate facing the drifting chamber 200 and is thus restricted to the part 341 to its certain volume.

So that the structural unit 210 of gas moving with the gas sample flow 100 entering the cell structure through the inlet 204 could change to the ion 301 in due course, when arriving to the ionisation section restricted by the broken lines 220 and 221, it 210 has to move on that side of the part 344 of the divider plate in the drifting chamber 200 which is indicated by the reference number 231, at least at the ionisator. The part 344 of the divider plate can have the electrode 308 integrated into its structure, or the plate part 344 itself can act as the electrode for generating the electric field. Ionisation can be based on corona discharge. In this case, for maintaining the corona discharge with the help of an electric field, the ionisation section has most preferably at least two electrodes 307 and 308, the corona discharge occurring between said electrodes due to the electric field between them as the strength of said electric field is generated by the sufficient potential difference between the electrodes 307 and 308.

In the cell structure in FIG. 3B, the drifting chamber 200 is limited by the planar part 322 and the plane 302. The part 302 can be formed in accordance with the figure, in which case it can have apertures for making possible a certain design of the flow channel. The support 318 is connected to the planar part 322 drawn in the figure for supporting the divider plate including the parts 323 and 344. For separating said divider plate from the part 302 belonging to the cell structure in the cell structure in FIG. 3B, it has a support part 317. The parts can most preferably be shaped for providing a gas flow channel for the input 204 and output 205 of the gas flow 100 so that also the wall part 354 of the channel can be used for the shaping. For fastening the electrodes in FIG. 3B, such insulating materials can be used in the selection of materials, that the resistivity, especially surface resistivity of which is stable and most preferably, as high as possible for eliminating leakage currents in the electric operating range of the electrodes.

The divider plate with the parts 343 and 344 can be made, for example, of stainless steel, capton, or PTFE. One possible insulating material can be stainless steel coated with a titanium nitride coating. It is especially suitable for space-technical applications, as it is inert and electrically stable. The use of the electric field in the ionisation section 202 can require that the electrode 308 be insulated from the divider plate. Upon using insulating material in the divider plate, the electrode 308 can be attached directly to it. FIG. 3B shows an electrode pair, a front field electrode pair, comprising the electrodes 323 and 324 for forming a specific front field. The electrodes in the area of the front field electrode pair belong to the front cell. The function of the front field of the front cell is to remove charge-carrying particles and/or ions from the gas sample that are inappropriate for the mobility analysis of ions so that they would not get deeper in the flow of direction to hinder the charging and thus also the forming of the mobility spectrum. In addition, the counter-electrode 324 of the front field can be utilised as a measuring electrode, and the signal obtained from it directly or the information to be formed on the basis of it can be used in the actual gas measurement and in the identification of ions.

FIG. 3B also shows a second electrode pair, a back field electrode pair, consisting of the electrode 333 and electrode 334, which belong to the back cell. The purpose of the back field electrode pair of the back cell is to provide an electric field, the back field, after the analysis electrode and behind it, and to make possible the realtime measurement of gas rate with the help of it. Because the collection efficiency of the analysis electrode pair depends on the voltage between its electrodes, it is possible that part of the ions will not be aggregated onto the analysis electrode pair. When voltage is coupled between the electrodes in the back field electrode pair, the ions that have not been aggregated to the analysis electrode can be collected with the help of the back field electrodes. The electric field generated by the actual analysis electrode pair can vary, for example, sinusoidally. In this case, the field strength and/or frequency of the back field can most preferably be bound to the respective quantities of the analysis voltage and, most preferably, the reference signal can also be utilised for forming the signal obtained from the back field, the back field signal. The aggregation of ions onto the back field electrode generates charge changes in it so that a back field signal can be formed from the back field electrode 344 analogically in a similar way as an analysis signal is formed from the analysis electrode 314. The shape of the back field signal can differ from the analysis signal, for example, due to distortion and/or phase shift. On the basis of the phase shift, it is then possible to determine the gas rate by comparing certain waveforms of the analysis signal and the back field signal with each other. In this case, the waveform of an analysis signal occurring in a certain time interval has a certain delay, which depends on the gas flow rate, before the respective waveform can be observed from the back field electrode in the back cell a certain time later. For example, a delay determination based on autocorrelation function can then be used. In this case, the flow rate of the gas flow 100 can be measured real-time together with the ion measurement. In addition, the back field signal can be processed, for example, with a measuring amplifier, which, however, has not been drawn to the FIG. 3B. Neither does the figure show other amplifiers (amplifiers or similar needed for amplifying and/or processing the analysis signal and reference signal) and/or voltage sources, nor means needed for controlling these, nor other means used, for example, for filtering the signals.

In the cell structure according to an embodiment of the invention, the geometry and size of the back field electrode pair are most preferably selected on the basis of the collection efficiency of the analysis electrode pair and the phase difference, and the allowable measurement error in it.

In the cell structure according to an advantageous embodiment of the invention, a back field electrode is a part of the disintegrated analysis electrode so that also the back field can be utilised in the identification.

In the measurement of gas rate performed with the help of the back field electrode pair, advantage is gained in relation to techniques based on pressure difference and mass flow measurements, for example, in that the method utilising the back field electrode is not dependent on the density and thus humidity of the sample gas and/or the concentration of the sample gas as in the methods based on mass flow and pressure difference measurements.

In the next example, the operation of the cell according to FIG. 3B is examined. The sample gas is taken along the drifting chamber 200 within the reach of the reference electrode pair and thus to the electric field between the electrodes in said electrode pair. The gas flows further past the ionisation section (the section of the drifting chamber 200 in part 341 limited between the extensions of the broken lines 220 and 221) so that the gas is ionised in a certain way which is determined by the properties of the ionisation source, charger. As the gas flow advances to the place of the analysis electrode pair to the electric field between the electrodes in the electrode pair, the generated ions can be analysed with the help of the electric field formed by the analysis electrode pair.

With a divider plate provided with the parts 343 and 344, it is possible to realise the cell structure of an advantageous embodiment according to the invention in accordance with the second order cell structure, but with a simple mechanical structure. In this case, the gas flow passing on the side of the divider plate 341 facing the charging part of the ionisation section is charged, as again the part of the gas flow passing on the other side 342 of the divider plate, is not charged. The portion of the volume flow of the charged gas relative to the volume flow of the uncharged gas can then be optimised to be most advantageous for the measurement accuracy by placing the divider plate to a suitable distance between the plates 302 and 322, substantially in their direction. In this case, the parts 317 and 318 of FIG. 3B can be arranged to correspond to different measurement geometries with a different ratio of the volume of charged gas to the volume of uncharged gas. It is then also possible to make the dimensions of the chamber 200A arrangeable and thus adjustable. The parts 317 and 318 can then also consist of several parts, these parts forming a certain tuning set for optimising the dimensions of the cell structure for a certain gas measurement. With the divider plate it is also possible to minimise flow mechanical interferences in the gas flow.

In according to an advantageous embodiment of the invention, the divider plate with the parts 343 and 344 can be provided with means for coupling voltage between the divider plate and a part in reference potential—for example ground potential—analogically, as to a gate of a radio tube of the triode type, in which case the voltage to be coupled to the divider plate can be used for controlling the moving of ions through the apertures of the divider plate to one analysis electrode in a similar way as the gate voltage of a radio tube is used for controlling the flow of electrons between anode and cathode.

C. A Number of Other Advantageous Embodiments

FIG. 4A presents a diagram, in which a device 400, a gas measuring device 400, according to an embodiment of the invention is shown as an example. This has the cell structure 200A that is shown in FIG. 3A. The gas measuring device 400 can also have the cell structure 300 according to FIG. 3B. Such a gas measuring device vice is illustrated in FIG. 4B. The gas measuring device 400 can also have a number of cell structures, in which each cell structure is then optimised for detecting the mobility of ions within a certain mobility range between a certain minimum mobility and a maximum mobility. By using several cell structures parallel, it is then possible to cover a wider mobility range than by using a single cell structure. The price to be paid is then that the number of control and other devices needed is increased and/or the control becomes more complicated. In this case, the device can also have cell structures of either type or both types, for optimising the mobility range. For example, one of the cell structures to be used in parallel can be arranged to identify positive ions and a second one to identify negative ions. It can also be stated that by using several cell structures in parallel in the measuring device, the redundancy of the measuring device can be increased, which is useful against failure situations. In addition, with the device of several cell structures it is possible to perform measurements, in which it is necessary to phase the mobility analysis of ions for identifying certain substances without, for example, having to rinse the chamber between analyses, which would be necessary, for example, with a device provided with a single cell structure in a respective situation. It is also possible to measure both positive and negative ions simultaneously from substantially the same environment.

The markings drawn to FIG. 4A in a gas measuring device 400 according to an advantageous embodiment of the invention have the first order cell structure 200A according to FIG. 3A, formed by an aspiration condenser. In this case, the markings in FIG. 4A in the cell structure have the reference cell 411, the ionisation section 410, and the analysis cell 409, in said order in the direction of advance of the gas sample along the analysis chamber.

As an example of an advantageous embodiment of the invention, with the markings drawn in FIG. 4B, the device 400, has a second order cell structure 300 according to FIG. 3B, formed by an aspiration condenser; the cell structure thus also having a divider plate. In this case, according to the markings of FIG. 4B there are reference cell 411, the ionisation section 410 and the analysis cell 409, in said order in the direction of advance of the gas sample along the analysis chamber. However, the cell structure of the device 400 in FIG. 4B then has a front cell 414 before the reference cell. The front cell is then most preferably realised with the help of a front field electrode pair consisting of the electrode 323 and the electrode 324, as is shown in connection of the cell structure 300 in FIG. 3B. In the example in FIG. 4B, still the back cell 415 has been shown of the cell structure, placed after the analysis cell 409 in the flow direction of the sample gas. The back cell is then most preferably realised with the help of a back field electrode pair comprising the electrode 333 and the electrode 334, as is shown in connection of the cell structure 300 in FIG. 3B. With the help of the back field electrode, it is possible to determine the average rate of the gas flow 100.

The front cell and/or back cell can also be eliminated from such a second order cell structure, which is illustrated in FIG. 3B. In such a case, the advantages offered by the cell-left-out from the cell structure and thus from the device are not achieved, but to counterbalance this, the cell structure in itself is simpler so that, on the other hand, space can be saved from the device 400.

The gas measuring device 400, according to an advantageous embodiment of the invention, has the microprocessor 406 for maintaining and controlling its 400 analysis and other functions and for processing the signals obtained from the reference and analysis electrodes. In addition, the device 400 can have specific means for processing the signal obtainable with the help of an electrode in the front and/or back field electrode pair in the cell structure 300, the means most preferably being programmatic.

In FIGS. 4A and 4B, there is shown the amplifier 412 for amplifying the signal coming from the reference cell 411; in the examples in Figures, the amplifier can be controlled by the microprocessor 406. In the figures, the amplifier 422 has also been drawn connected to the analysis cell 409. However, an amplifier can also be connected to the front cell 414 and/or back cell 415 drawn in FIG. 4B for amplifying a signal and/or for processing the available signals, although such are not shown in FIG. 4B. In this case, the amplifier in question can most preferably be controlled by the microprocessor 406, at least in part.

The amplifiers 412 and 422 have been drawn connected to the comparator means 407, which is also in contact with the microprocessor 406. The comparator means 407 can have several inputs, for example, one for each signal obtainable from the electrode of a cell. The comparator means 407 can also comprise signal processing means for processing an incoming signal, which most preferably have been arranged ultimately for optimising the identification of ions. The comparator means 407 is in contact with the microprocessor 406 for feeding the analysis signal coming through the comparator means to the microprocessor for actions to be performed with it.

In FIGS. 4A and 4B there is a drawn amplifier 412 connected to the comparator means 407, and by a bi-directional connection to the microprocessor 406 so that a reference signal can be directly obtained from the amplifier 412 to the microprocessor 406 suitably amplified and formed to digital form, as its 412 one output has the necessary analogue to digital converter. The reference signal can be obtained to the microprocessor 406 also through the comparator means 407. Respectively, also a signal originating from the electrode of some other cell 409, 410, 414, 415 can be amplified and routed, when necessary, directly to the microprocessor 406 in digital form, or the signal can be routed through the comparator means 407, for example, for connecting the signal to other signals or parts of these in a particular way.

From each amplifier, with which a signal to be obtained from a cell 409, 410, 411, 414, 415 is amplified, but of which only the amplifiers 412 and 422 have been drawn in the FIGS. 4A and 4B, there can be provided a connection to a separate input in the comparator means 407. For example, the comparator means 407 can have an analogue input and a digital output. In this case, a microprocessor 406 can be used to control the functions of the comparator means 407 for processing the signal, which can be performed also programmatically in the microprocessor, when applicable, for saving space and/or components.

The microprocessor 406 and some software means operating in it can then be used for analysing the analysis signal, for processing it, for example, by filtering and to form the mobility spectrum of ions. On the basis of the mobility spectrum, the type of ions incorporating into the mobility spectrum can be identified. Most preferably, the microprocessor 406 also has a connection to some memory means for saving necessary programs, control parameters and/or other data used in the identification, although the examples in FIGS. 4A and 4B do not separately show the memory in the device 400. Most preferably, the identification of ions is based on librarised data, which can form a database, which can be, for example, a relational database.

In the device 400, according to an advantageous embodiment of the invention, there are further provided the transmitter-receiver means 404 for controlling the analysis operation and preferably also an antenna 403 or similar for maintaining the functional control connection between the device 400 and the device 401 controlling it and/or the operator. In this case, the microprocessor 406 is most preferably connected also to the transmitter-receiver means 404 so that data transmission just between these is possible.

In FIGS. 4A and 4B, a mobile station has been drawn as the controlling device 401, but it can also be some other radio device, for example, a radio telescope in space-technical applications, or an infrared transmitter. In this case, the message 402 intended to travel between the gas measuring device 400 and its controlling device 401 can comprise an impulse for controlling the gas measuring device 400 or, as a response to an impulse, a report on the measuring results and/or the status of the gas measuring device 400 to be received, for example, with the device 401. An impulse can then be used for commanding the device 400 to set certain values for the quantities influencing the analysis operation as a response to said impulse. Such quantities, as the voltage between the electrodes in the electrode pair of a certain cell, its waveform and/or frequency can be given as an example.

In FIG. 4A it has been shown that the microprocessor 406 is in contact with the control means in the voltage sources 405 and/or 413, and in FIG. 4B, in the voltage sources 423 and/or 425. In this case, a control means, which most preferably is in the voltage source 405, 413, 423, 425 as its part, can be arranged for controlling one or several parts of the cell structure; for example, the reference cell 411, the ionisation section 410, the analysis cell 409, the front cell 414 and/or the back cell 415 according to the controls of the microprocessor 406. The voltage sources 405, 413, 423, 425 used in the cells and/or the ionisation section for forming the necessary voltages most preferably comprise said control means. Each control means has the necessary number of inputs for controlling the output voltages of a certain voltage source. The polarity of the output voltage of a certain voltage source, its nominal voltage, amplitude, waveform and/or frequency are most preferably controllable in an independent way according to the need of the cell in each cell structure for making possible the reliability of a certain level for the identification of ions.

In FIG. 4B, the voltage source 423 is drawn to have a different number of outputs implemented for the feeding of parts of the cell structure from the voltage source 413 in FIG. 4A. In FIG. 4B, the voltage source 425 is drawn to have a different number of outputs from the voltage source in FIG. 4A implemented for the feeding of parts of the cell structure. Because of this, the reference numbers for the voltage sources are different between FIGS. 4A and 4B, although the voltage sources as such would have no other difference.

The gas measuring device 400 can also be set to report data concerning its own status and/or send analysis results, and to use a certain form of communications for sending these. The device can be a device intended to be fixedly installed in a laboratory, a device suitable for cross-country and/or a portable device intended to be used on Earth for the identification of certain gaseous substances. The device can also be arranged for the identification of gases in mine conditions, tunnels, a space ship, a submarine, or some other space, for example, in a laboratory or fume hood, in which the composition of the gases has significance.

FIG. 5 illustrates a method according to an advantageous embodiment of the invention for identifying the electric mobility of ions of the carrier gas with the help of electric fields. In this case, a first electric field is formed between a first reference electrode and a second reference electrode (500A), and a second electric field is formed between a first analysis electrode and a second analysis electrode (500B).

After the electric fields have been formed, a gas sample is taken (501) in the method, which gas sample is processed (502), for example, to remove particles, but also heavy or light ions can be removed from it, which as such can have a detrimental influence on the analysis accuracy and/or the cell structure as such. The particles to be removed can be solid and/or liquid material. The forming of electric fields can also be interpreted so that an electric field is changed from a first state to a second state different than said first state. In addition, most preferably as a continuous method, it can have several phases in progress at least in part simultaneously.

In the method, the sample gas is first directed through the reference cell for producing a reference signal, the sample gas is charged to be electrically charged in said ionisation section for providing a certain electric charge to a certain relative part of the number of structural units of the sample gas, and as the sample gas flows further to the analysis cell after the ionisation section, the ions in the sample gas are analysed, based on their electric mobility.

The sample gas is analysed (503) for producing a first signal, on the one hand, on a reference electrode and, on the other hand, for forming a second signal on an analysis electrode, on the basis of changes of charge in the reference electrode and analysis electrode. Also charging the sample gas in the ionisation section relates to the analysis, the ionisation section being located between the reference section and the analysis section. The mentioned first and second signals are processed (504) for generating a processed signal, on the basis of which a mobility spectrum is provided, which is used in the identification (505) of the ion. For example, a suitable deconvolution algorithm can be used in the identification. The identification can also be based on librarised data or a similar database of the mobility spectrum. In addition, the mobility spectrum to be formed on the basis of the processed signal can be reported forward either before or after the identification, on the basis of a functional data transmission connection, for example by way of a radio. It is also possible to send merely the processed signal for performing the identification itself in a disintegrated manner, for example, outside the means or a similar device processing the signal. The disintegrated analysis can be advantageous, for example, in a space-technical application or in such a case in which the cell structure itself is either far away and/or in a closed space for analysing hazardous substances.

In a method according to an advantageous embodiment of the invention, the particle-shaped solid and/or liquid material can be removed by vaporisation. In this case, the temperature of the cell structure has to be kept constant so that all the material arriving at the analysis cell of the cell structure is most preferably in gas phase. For reducing the changes caused by particles on electrode surfaces, for example, at least the analysis cell can be rinsed with a particle-free neutral gas, for example, in a cyclic measurement in which sample gas is measured for part of the time and rinsed for part of the time.

As an example of the preferable dimensions of the cell structure according to an embodiment of the invention it can be stated that the height of the drifting chamber of the cell structure, referring to the distance between the electrodes in the electrode pair (for example, 313 and 314) is about 0.1-10 mm for a drifting chamber with first or second order cell structure according to an advantageous embodiment of the invention. With the chamber of second order, the distribution plate is most preferably within a distance of 0.05-9.95 mm from an analysis electrode. In the cell structure according to an advantageous embodiment of the invention, the gas flow rate is approx. 0.1-10 l/min. The detailed selection of the flow rate depends on the ion flux, the geometrical dimensions of the cell structure and/or device in general, and the pump required for maintaining the flow. Table 1 shows examples of the use parameters for some advantageous embodiments according to the invention. The Table do not mention a free waveform, which can be presented with the help of an exponential function based signals by combining them. TABLE- US-00001 TABLE 1 Examples of the use parameters of some advantageous embodiments according to the invention for first and/or second order cell structures Cell The electric field of the cell structure Frequency Amplitude Direct voltage type (Hz) Waveform (|V|) component (|V|) Front cell 0 or 1-1000 DC or sine, tri-12 12 or 0 (when the angle, ramp signal is not DC) Reference 1-1000 Sine, triangle, 12 0 cell ramp Analysis 1-100 Sine, triangle, 12 0 cell ramp Back cell 0 or 1-1000 DC or sine, tri-12 12 or 0 (when the angle, ramp signal is not DC).

The invention claimed is:

1. A method for an identification of substances in a flowing gas, based on electrical mobility of ions comprising:
   (a) setting a first electric field between electrodes in a reference electrode pair;
   (b) setting a second electric field between electrodes in an analysis electrode pair;
   (c) transporting a gas sample through the reference electrode pair, an ionization section and the analysis electrode pair in said order;
   (d) analyzing the gas sample;
   (e) forming a mobility spectrum of ions; and
   (f) identifying an ion from the gas sample on the basis of the mobility spectrum.

2. A method according to claim 1, wherein changes in charge on the electrodes in the reference electrode pair are observed to thereby form a reference signal, said gas sample is charged for generating ions, and the changes in charge on the electrodes in the analysis electrode pair are observed to thereby form an analysis signal.

3. A method according to claim 1, wherein the mobility spectrum is formed on the basis of a reference signal and an analysis signal generated by said first and second electric fields, respectively.

4. A method according to claim 1, further comprising preprocessing the gas sample to thereby remove particulate solids or liquid materials before the sample arrives at the reference electrode pair.

5. A method according to claim 1, wherein identifying said ion a mobility library or a respective database.

6. A method for electrically determining gas flow velocity in an aspiration condenser, comprisings condenser,
   (a1) setting a first electric field between electrodes in a first electrode pair comprising a first electrode;
   (a2) setting a second electric field between electrodes in a second electrode pair, comprising a second electrode;
   (a3) setting a third electric field between electrodes in a third electrode pair comprising a third electrode;
   (a4) observing changes of charge of the first, second and third electrode in said first, second and third electric field;
   (a5) correcting changes of charge detected, using said second electrode and said third electrode, on the basis of the changes of charge detected on the first electrode;
   (a6) determining the time, passing between the occurrence of changes of charge on the second electrode and on the third electrode; and
   (a7) calculating the gas velocity,
   wherein said aspiration condenser comprises a cell structure having a flow channel for controlling the gas flow, a reference cell arranged to form a reference signal, an ionization section for achieving an ionization effect into the sample gas, and an analysis cell arranged to form an analysis signal so that the reference cell, the ionization section, and the analysis cell are located in said order in the direction of flow of the gas.

7. A method according to claim 6, wherein an autocorrelation function is formed for determining the time between the detected changes of charge on the second and third electrode.

8. A method for identification of substances in a flowing gas sample as based on a cell structure and ion mobility of the ions, comprising:
   controlling the gas flow by a flow channel in the cell structure;
   forming a reference signal;
   achieving an ionization effect into the gas sample;
   forming an analysis signal,
   wherein said forming the reference signal, achieving the ionization effect and forming the analysis signal are implemented by a reference cell, an ionization section and an analysis cell, respectively said reference cell, said ionization section, and said analysis cell, being arranged into said order in the flow channel.

9. The method of claim 8, wherein
   a first electric field is set between electrodes in a reference electrode pair,
   a second electric field is set between electrodes in an analysis electrode pair,
   the gas sample is taken to be transported through the reference electrode pair, the ionization section, and the analysis electrode pair in said order,
   the gas sample is analyzed,
   a mobility spectrum of ions is formed, and
   an ion is identified from the gas sample on the basis of the mobility spectrum.

10. The method of claim 9, wherein, in analyzing the gas sample, changes of charge on the electrodes in the reference electrode pair are observed to thereby form a reference signal, the gas sample is charged to generate said ions, and changes of charge on the electrodes in the analysis electrode pair are observed to thereby an analysis signal.

11. The method of claim 9, in which said mobility spectrum is formed on the basis of the reference signal and the analysis signal.

12. The method of claim 9, further comprising pre-processing the gas sample to remove solid or liquid material before the gas sample arrives at the reference electrode pair.

13. The method of claim 9, in which identifying said ion from said gas sample is based on a mobility library or a respective database.

* * * * *